US005708029A

United States Patent [19]
Vanmoor

[11] Patent Number: 5,708,029
[45] Date of Patent: Jan. 13, 1998

[54] HIGH BLOOD PRESSURE RELIEF METHOD AND COMPOSITIONS

[76] Inventor: Arthur Vanmoor, 153 E. Palmetto Park Rd. #219, Boca Raton, Fla. 33432

[21] Appl. No.: 559,758

[22] Filed: Nov. 13, 1995

[51] Int. Cl.$^6$ ............................ A61K 31/195; C07C 229/06
[52] U.S. Cl. ................................................ 514/562; 562/553
[58] Field of Search ................................... 514/562, 563, 514/564, 566

[56] References Cited

U.S. PATENT DOCUMENTS 4,902,718   2/1990   Bayless et al. .................... 514/562

OTHER PUBLICATIONS

Sebranek, J.G. et al.: Physiologicl Role of Dietary Sodium in Human Health and Implications of Sodium Reductions in Muscle Foods. Food Technology, pp. 51–59, Jul. 1983.

Murray, R.H.: Blood Pressure Responses to Extreme Sodium Intake in Normal Man. Proc. Soc. Exp. Biol. Med. vol. 159, pp. 432–436, 1978.

Zandberg, P.: Animal Models in Experimental Hypertension: Relevance to Drug Testing and Discovery. Handbook of Hypertension, vol. 3, pp. 1–33, 1984.

Patel, A. et al.: L–Arginine Administration Normalizes Pressure Natriuresis in Hypertensive Dahl Rats. Hypertension, vol. 22, pp. 863–869, 1993.

Tsuji et al.: Antihypertensive Activities of Benikoji Extracts and Gama–Aminobutyric Acid in Spontaneously Hypertensive Rats. Eiyogaku Zasshi, vol. 50, pp. 285–291, 1992.

Ohnuki, N. et al.: Effects of L–Cysteine on Blood Pressure in Hypertensive Rats and Some Aspects of its mechanism. yakasi to Chiryo, vol. 15, pp. 1195–1201, 1987.

Tobian, L.: NaCl–Related Hypertensions. Hypertension Edited by Ong and Lewis, pp. 96–97 and 115, 1984.

*Primary Examiner*—C. Warren Ivy
*Assistant Examiner*—Charanjit S. Aulakh
*Attorney, Agent, or Firm*—Otto S. Kauder

[57] ABSTRACT

Disclosed is the method of determining the effectiveness of an agent for the relief of elevation of the blood pressure, comprising the steps of a) administering to a susceptible subject a quantity of a trigger substance reproducibly effective in producing within a period of six hours a perceptible increase in blood pressure lasting for at least twenty-four hours in the absence of treatment, b) administering to said subject having received said quantity of trigger substance a predetermined quantity of the agent whose effectiveness is to be determined, c) measuring the duration of said elevation of blood pressure upon administering said agent, and d) comparing the duration of said elevation with and without the administration of said agent.

Also disclosed are effective quantities of certain nutrient substances which can reproducibly relieve elevated blood pressure produced in a susceptible subject by the administration of a trigger substance.

29 Claims, No Drawings

HIGH BLOOD PRESSURE RELIEF METHOD AND COMPOSITIONS

This invention relates to the relief of elevated blood pressure, also known as hypertension. More particularly, this invention relates to the relief of arterial hypertension defined as elevation of systolic and/or diastolic blood pressure, either primary (essential hypertension) or secondary (see Merck Manual, 16th edition, 1992, pages 413–429). As stated in this reference work, "primary or essential hypertension is of unknown etiology, and it seems improbable that a single cause will explain its diverse hemodynamic and pathophysiologic derangements. Heredity undoubtedly predisposes individuals to hypertension, but the exact mechanism is unclear." It has been estimated that there are more than 50 million hypertensives in the United States, that is persons with systolic blood pressure of 140 millimeters of mercury or more and/or diastolic blood pressure of 90 mm or more, or taking antihypertensive medication.

Primary hypertension is asymptomatic until complications develop. Symptoms and signs are non-specific and arise from complications in target organs. Complications include left ventricular failure; atherosclerotic heart disease; retinal hemorrhages, exudates, papilledema, and vascular accidents; cerebrovascular insufficiency with or without stroke, and renal failure.

As to treatment, the same reference states that "there is no cure for primary hypertension, but therapy can modify its course." In cases of mild hypertension, non-drug therapies such as weight reduction to ideal levels, modest dietary sodium restriction to less than 2000 milligrams per day, limitation of alcohol intake to less than one ounce of ethanol per day and prudent exercise can make drug therapy unnecessary. However, it is recommended that "when complications are present or impending, or when the diastolic blood pressure is greater than 95 mm, drug therapy should not be deferred while awaiting the uncertain results of dietary therapy." The goal of drug therapy is stated to be reducing the blood pressure to normal, ie 140/90 or less.

Recommended antihypertensive drugs include four major classes of agents, identified as diuretics, beta-blockers, calcium antagonists, and angiotensin-converting enzyme inhibitors. The reference lists 19 different diuretics grouped in three subclasses, 13 different beta-blockers, nine different calcium antagonists grouped in three subclasses, and five different antiotensin-converting enzyme inhibitors. The choice among these many agents is said to be based on the patient's age, race, and the presence or absence of particular complications and conditions associated with high blood pressure.

From the 1988 Report of the Joint National Committee on Detection, Evaluation, and Treatment of High Blook Pressure (Archives of Internal Medicine, 1988, vol 148, pages 1023–1038) the reference reproduces a "stepped care therapy" scheme for hypertension which suggests trying a non-drug approach first; then, as a second step, a drug from the above indicated classes; then as a third step increasing the dose of the first drug, substituting a drug of another class, or adding a second drug; as a fourth step, adding a third drug of a different class or making a substitution for the second drug, and, if necessary, adding a third or fourth drug; and ultimately "evaluate further and/or refer; consider step-down therapy and continue non-drug approaches." The large number of choices, and the far from categorical promise of success, coupled with the fact that the listed drugs are not free of unpleasant and even dangerous side effects, provides clear evidence that new and improved remedies for high blood pressure are still needed.

The available drugs have been discovered by the methods of classical pharmacology, which while sometimes highly successful are always complex, laborious, time-consuming and costly. For an overview of the entire process from the proposal of an idea by a researcher to the initiation of clinical trials of a remedy, reference can be had to "Natural History of a Typical Drug" a chapter by Dr. E. L. Harris in "The Principles and Practice of Clinical Trials" (Harris and Fitzgerald, editors, E. & S. Livingstone, Edinburgh and London, 1970). Harris writes "The first stage is that of the idea. Whatever the source of the idea, it is considered by a research panel consisting of medical, chemical, pharmacological, pharmaceutical and commercial interests. If the panel feel that the idea has merit, then the research chemist sets about synthesising the compound or a number of related compounds. This can be a very long and arduous task; it has been estimated that synthesis and initial biological screening of a single compound can take up to 400 man hours to achieve . . .

When sufficient quantities have been made the pure drugs are handed over to the pharmacologist who carries out a programme of empirical screening tests, designed to cover as wide a range of pharmacological actions as economically as possible so as to expose any effects which might be of therapeutic use. If an anction is detected more detailed experiments to elucidate this are carried out.

Many compounds are rejected at this stage either because of lack of activity or gross toxicity. Those that do survive are again considered by the research panel who decide whether the agent has sufficient promise to go forward to assess its safety in animals.

There are three phases in toxicity testing. The first is the acute toxicity study which deals with the quantitative assessment of the short term effects of a drug. The response is noted after a single oral or parenteral dose, or several doses given within 24 hours. These tests are carried out in a variety of species.

The next is sub-acute toxicity, and in general covers repeated dosage in at least two species, such as mice and rats, for periods up to 90 days. An additional non-rodent species, eg. dog, is often included.

Chronic studies are for the duration of life in the animal—rats and mice are suitable. Occasionally long term studies are employed in other animals such as dogs and monkeys for periods up to two years . . .

When the exacting toxicological studies are completed and the research panel is satisfied with all the data that has been generated, the drug is administered to healthy volunteers . . ."

SUMMARY OF THE INVENTION

In accordance with this invention, I have found that I can reproducibly cause a susceptible human subject to experience a measurable and reproducible increase in blood pressure within a short period of time upon the oral administration of a sufficient quantity of any of a class of substances which I propose to call trigger substances. These trigger substances are in widespread consumer use and are without effect on the great majority of the human population. in a susceptible subject, such as myself, however, the effect is both reproducible and sufficiently long lasting to serve as research tool for the evaluation of agents effective in relieving hypertension. Accordingly, the method of determining the effectiveness of an agent for the relief of pain comprises the steps of a) administering to a susceptible subject a quantity of a trigger substance reproducibly effective in producing within a period of six hours a perceptible increase in blood pressure lasting for at least twenty-four hours in the absence of treatment, b) administering to said subject having received said quantity of trigger substance a predetermined quantity of the agent whose effectiveness is to be determined, c) measuring the duration of said elevation of blood pressure upon administering said agent, and d) comparing the duration of said elevation with and without the administration of said agent.

Also in accordance with this invention, I have found that effective quantities of certain nutrient substances can reproducibly reduce to normal levels the elevated blood pressure produced in a susceptible subject by the administration of a trigger substance in less time than required by a conventional remedy. Being nutrient substances that are ingested and metabolized by humans daily, such substances are inherently safe. Accordingly, the method of relieving hypertension in a person in need of such relief, comprises the administration to such person of a quantity of an agent determined to be effective in relieving hypertension by the method of this invention. Such administration of an agent can take place after the administration of a trigger substance, at the same time as a trigger substance is administered, or even before a trigger substance is administered, so that the increase in blood pressure that would be produced without the agent is thereby prevented.

Also in accordance with this invention, I have found that an agent found effective in accordance with this invention in relieving hypertension can be combined with a pharmaceutically acceptable carrier to provide an effective palatable high blood pressure relief remedy composition. Moreover, I have found that a combination of two or more selected agents found effective in accordance with this invention in relieving hypertension can be combined with a pharmaceutically acceptable carrier to provide a pleasant tasting as well as effective and palatable high blood pressure relief remedy composition.

DESCRIPTION OF PREFERRED EMBODIMENTS

Trigger Substances

A trigger substance according to this invention is defined as any substance that, when administered to a susceptible human subject, reproducibly gives rise to an elevation of systolic and/or diastolic blood pressure in such subject in a time period of six hours or less. Preferred trigger substances are those known to be safe to administer to a human subject, particularly substances known to be in consumer use or authoritatively regulated for such use under observance of appropriate limitations. Included among such trigger substances are certain common foods and substances commonly added to foods as seasoning, such as table salt. Also included are substances known to lead to elevated blood levels of cholesterol. It is well known that elevated cholesterol levels can lead to narrowed arteries and elevated blood pressure, but such changes occur slowly over many years. An immediate effect of such cholesterol increasing agents on blood pressure within six hours has not previously been reported.

Trigger substances can also include whole products in which it may or may not be possible to identify a particular ingredient as responsible for the trigger effect. Such products include chopped beef, many kinds of manufactured meat products such as sausages, and hamburger meat as served in many large fast food chain establishments. Whether the trigger substance in such meats and meat products be the meat itself or minor constituents possibly contained therein, or a combination of both, or neither of these, is less important than that a reproducible trigger effect has been observed.

The quantity of trigger substance to be administered for elevation of the blood pressure to be reproducible is readily determined empirically. For example, a reproducible increase in both systolic and diastolic blood pressure has been noted by a susceptible individual upon consumption of one hundred grams of bologna sausage.

Agents Effective in Relieving Elevated Blood Pressure

In accordance with this invention, any desired agent can be tested for its effectiveness in shortening the duration of elevated blood pressure produced in a susceptible individual by administration of a trigger substance and hastening its return to a normal level. The only limitation is the practical requirement of not doing harm to such individual. For that reason, I have sought effective agents principally among substances known to be safe to administer to a human subject, particularly substances known to be nutrients ingested and metabolized by human beings on a daily or at least frequent basis. I have tested many nutrient substances and found effective among these a restricted group of water soluble aminocarboxylic acid compounds at dose levels in the range from 200 to 20000 milligrams. I use the term water soluble to refer to a solubility of at least three grams in 100 ml of water at 25° C.

A preferred group of water soluble aminocarboxylic acid compounds effective according to this invention in relieving hypertension can be represented by formula (I):

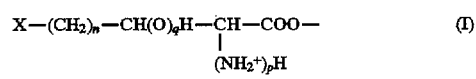

$$X-(CH_2)_n-CH(O)_qH-CH-COO- \quad (I)$$
$$| $$
$$(NH_2^+)_pH$$

in which X is selected from the group consisting of —SH, —CONH$_2$, —N(CH$_3$)$_{3+}$, —SCH$_3$, —NH$_2$,

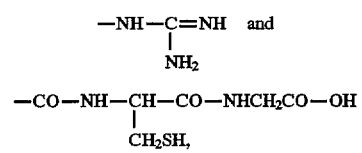

$$-NH-C=NH \text{ and}$$
$$|$$
$$NH_2$$

$$-CO-NH-CH-CO-NHCH_2CO-OH$$
$$|$$
$$CH_2SH,$$

n is zero, one, two, or three, and p and q are each zero or one, provided that p is zero and q is one only when X is —N(CH$_3$)$_{3+}$.

Table 1 which follows includes particularly preferred water soluble aminocarboxylic acid compounds represented by formula (I) which I have found effective in relieving hypertension when administered after administering a trigger substance and in preventing hypertension when administered before administering a trigger substance.

TABLE 1

| # | Name | X | n | p | q |
|---|------|---|---|---|---|
| 1 | 2-amino-3-mercapto-propanoic acid | —SH | 0 | 1 | 0 |
| 2 | 2-amino-4-carbamoyl-butanoic acid | —CONH$_2$ | 1 | 1 | 0 |
| 3 | 2-amino-4-methylthio-butanoic acid | —SCH$_3$ | 1 | 1 | 0 |
| 4 | 2,5-diaminopentanoic acid | —NH$_2$ | 2 | 1 | 0 |
| 5 | 2,6-diaminohexanoic acid | —NH$_2$ | 3 | 1 | 0 |
| 6 | 2-amino-5-guanido-pentanoic acid | —NH—C(=NH)—NH$_2$ | 2 | 1 | 0 |
| 7 | 2-(4-amino-5-carboxypentano-amido)-3-mercapto-N-carboxymethylpropanamide | —CO—NH—CH(CH$_2$SH)—CO—NHCH$_2$CO—OH | 1 | 1 | 0 |
| 8 | 3-hydroxy-4-trimethyl-ammoniobutanoate | —N(CH$_3$)$_3$+ | 1 | 0 | 1 |

Formula (I) and all the effective compounds listed in Table 1 contain an assymetric carbon atom and hence exist in non-superimposable optically active forms (so-called D and L forms) and in racemic mixtures or DL forms. Both D and L forms of the effective compounds and racemic mixtures thereof are contemplated in accordance with this invention.

There is nothing about the structures of the effective compounds of this invention or their known nutrient properties that would have enabled one to predict their effectiveness in relieving hypertension in accordance with this invention. This unpredictability is further underscored by the finding that a number of aminocarboxylic acid compounds structurally similar to those effective according to this invention but not structured according to formula (I) are ineffective. In Table 2 following, there are listed a number of aminocarboxylic acid compounds found ineffective in relieving hypertension when administered after administration of a trigger substance. Some of these compounds can be represented by formula (II)

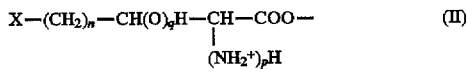

in which the assignments of X and/or n differ from those in formula (I)

TABLE 2

| # | Name | X | n | p | q |
|---|------|---|---|---|---|
| A | 2-aminopropanoic acid | hydrogen | 0 | 1 | 0 |
| B | 2-amino-3-phenylpropanoic acid | phenyl | 0 | 1 | 0 |
| C | 2-amino-3-imidazolyl-propanoic acid | imidazolyl | 0 | 1 | 0 |
| D | 2-aminoacetic acid | not applicable | not applicable | 1 | 0 |
| E | 2-aminopentanedioic acid | —COOH | 2 | 1 | 0 |

While these substances are ineffective in relieving hypertension, they do not act as trigger substances and thus can be present in modest amounts as companion substances to effective agents according to this invention. In this way such substances can contribute to the useful properties of the effective agents by enhancing their speed of action, palatability and/or taste characteristics. When present as companion substances to effective agents their concentration will typically range from 1 to 10 weight percent of the effective agent.

Palatable Oral Dosage Forms

Also in accordance with this invention, a pharmaceutically acceptable carrier can be combined with effective amounts of an effective agent according to this invention to provide a palatable oral dosage form for administering to a person in need of relief from hypertension. Accordingly, palatable oral dosage forms according to this invention comprise at least one pharmaceutically acceptable carrier and an effective amount of an effective agent according to this invention. Preferably the effective agent is an aminocarboxylic acid nutrient compound having formula (I). Particularly preferred effective agents are those listed in Table 1.

One preferred palatable oral dosage form according to this invention is a tablet. A particularly preferred tablet according to this invention comprises a high percentage of at least one aminocarboxylic acid nutrient compound having formula (I) and minor amounts of carrier material acting as binder for the tablet. Suitable binder materials include naturally occurring carbohydrates such as cellulose, starch, galactomannan, fructose, lactose, and sucrose; finely divided ingestible mineral substances such as calcium and magnesium carbonates, calcium and magnesium silicates, calcium and magnesium phosphates, alumina hydrates and hydrotalcite; waxy materials such as beeswax, stearin, stearates of calcium, magnesium, and aluminum, microcrystalline wax and paraffin, and mixtures thereof.

Another preferred palatable oral dosage form according to this invention is a capsule. Capsules have the advantage of delivering the effective agent directly to the alimentary canal without being tasted in the mouth. Suitable capsules are commercially available and are typically made of gelatin, but any sufficiently pure water soluble polymer can be used. Preferably the capsule is filled with the pure aminocarboxylic acid nutrient compound having formula (I); alternatively, suspensions of aminocarboxylic acid nutrient compound having formula (I) in a liquid carbohydrate such as corn syrup or honey, or in a lipid such as lecithin or canola oil can be encapsulated.

A further palatable oral dosage form according to this invention comprises an effective amount of an effective agent according to this invention in a liquid carrier such as a fruit flavored drink.

Preferably the effective agent is an aminocarboxylic acid nutrient compound having formula (I). Particularly preferred effective agents are those listed in Table 1.

Suitable fruit flavored drinks include natural fruit juices such as pineapple juice, apple juice, grape juice, orange juice, grapefruit juice, cranberry juice, and mixtures thereof; reconstituted juices prepared from water and fruit juice concentrates, and fruit juice drinks containing water and at least 10% of natural fruit juice.

In oral dosage forms according to this invention, the proportions of carrier to effective agent can vary over a broad range in accordance with the kind of carrier selected and the strength desired. Thus the proportion of carrier can be as little as 0.1% by weight, as in a tablet, and as high as 85% or even more, as in a fruit flavored drink.

Tablets in accordance with this invention can be prepared, for example, from 750 milligrams of each of compounds #1, 3, 5, 7, and 8 of Table 1 and 5 milligrams each of stearin, magnesium stearate, and magnesium silicate.

Capsules in accordance with this invention can be prepared, for example, by filling elliptical capsules of 1.5 ml capacity with 500 milligrams of each of compounds #1, 2, 3, 4, 5, 6, 7, and 8 of Table 1.

Fruit flavored drinks in accordance with this invention can be prepared, for example, from 3750 milligrams of each of compounds #1, 2, 3, 4, 5, 6, 7, and 8 of Table 1 and 75 milliliters of commercially available apple-cranberry drink.

Pleasant Tasting Oral Dosage Forms

Also in accordance with this invention, a pharmaceutically acceptable carrier can be combined with effective amounts of an effective agent according to this invention and a flavorant to provide a pleasant tasting oral dosage form for administering to a person in need of relief from hypertension. Accordingly, pleasant tasting oral dosage forms according to this invention comprise at least one pharmaceutically acceptable carrier, an effective amount of an effective agent according to this invention, and a flavorant. Preferably the effective agent is an aminocarboxylic acid nutrient compound having formula (I). Particularly preferred effective agents are those listed in Table 1.

Preferred flavorants that can be used in a pleasant tasting oral dosage form according to this invention include herbs such as basil, cilantro, dill, oregano, tarragon, and thyme; spices such as cinnamon, clove, ginger, mace, and nutmeg, and essential oils such as oil of lemon, oil of orange, oil of peppermint, and oil of sassafras.

In a particularly preferred pleasant tasting oral dosage form according to this invention, there are present in amounts selected to complement the taste characteristics of each at least one first nutrient compound having the formula $$X-(CH_2)_n-CH(O)_qH-CH-COO-$$
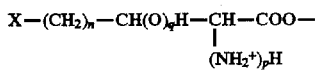

in which X is selected from the group consisting of —NH$_2$, and

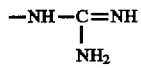

n is two or three, p is one and q is zero, and at least one second nutrient compound having the formula

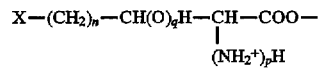

in which X is selected from the group consisting of —SH, —CONH$_2$, —N(CH$_3$)$_{3+}$, —SCH$_3$, and

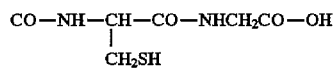

n is zero or one, and p and q are each zero or one, provided that p is zero and q is one only when X is —N(CH$_3$)$_{3+}$.

In such compositions, the taste characteristics of the first nutrient compound and the second nutrient compound interact in such a way as to produce an overall pleasant tasting composition.

Pleasant tasting tablets in accordance with this invention can be prepared, for example, from 750 milligrams of each of compounds #1, 3, 5, 7, and 8 of Table 1, 5 milligrams each of stearin, magnesium stearate, and magnesium silicate, and 10 milligrams of finely powdered cinnamon.

A pleasant tasting fruit flavored drink in accordance with this invention can be prepared, for example, by blending 4500 milligrams of each of compounds #1, 3, 5, 7, and 8 of Table 1, 110 milliliters of commercially available chilled grapefruit juice, and 5 drops oil of orange.

Pleasant tasting tablets containing a first nutrient compound and a second nutrient compound in accordance with this invention can be prepared, for example, from 500 milligrams of each of compounds #1, 2, 3, 5, 7, and 8 of Table 1, 250 milligrams of each of compounds #4 and 6 of Table 1, and 5 milligrams each of stearin, magnesium stearate, and magnesium silicate.

The following Examples are provided to illustrate the invention without intending to limit its scope, which is defined by the appended claims.

EXAMPLE 1

Quantities of hamburger meat as served in large fast food chains were fed on alternate days on an empty stomach and in the absence of other foods to a male human subject known to be susceptible to elevation in blood pressure believed to be associated with the consumption of meat products. The following observations were recorded

| | | Blood pressure reading at time shown: | | | |
|---|---|---|---|---|---|
| Trial | Quantity | before eating | ½ hour after | 2 hours after | 4 hours after |
| a | 75 grams | 140/90 | 155/92 | 160/95 | 160/95 |
| b | 150 | 140/90 | 160/95 | 170/100 | 170/100 |
| c | 225 | 140/90 | 170/90 | 190/105 | 190/105 |

The results show that the quantities of hamburger meat given in these trials are clearly sufficient to trigger a marked dose-related increase in blood pressure in this individual.

EXAMPLE 2

Quantities of bologna sausage were fed on alternate days on an empty stomach and in the absence of other foods to a female human subject whose normal blood pressure was 140/85. The following observations were recorded.

| Trial | Quantity | Blood pressure 2 hours after eating |
|---|---|---|
| a | 50 grams | 150/90 |
| b | 100 | 160/95 |
| c | 200 | 175/100 |
| d | 300 | 185/105 |

The results show that the quantities of bologna sausage given in these trials are clearly sufficient to trigger a marked increase in blood pressure in this individual.

EXAMPLES 3–4 and COMPARISON TRIALS 1–4

In each of the following trials, a 150 gram quantity of hamburger meat as served in large fast food chains was fed on alternate days on an empty stomach and in the absence of other foods to the same male human subject as in Example 1. After the onset of increased blood pressure was noted, approximately two hours after eating, there was administered a dose of a substance as noted below.

| Example no. | Substance | Dose | Time from administration to return of blood pressure to normal |
|---|---|---|---|
| 3 | Blend of substances from Table 1 | 2000 mg | 3 hours |
| 4 | Blend of substances from Table 1 | 4000 mg | 1 hour |
| Comparison 1 | none | | |
| Comparison 2 | blend of substances from table 2 | 4000 | no effect in ten hours |

The results show the blend of substances shown in Examples 3 and 4 was an effective agent according to this invention in relieving elevated blood pressure triggered by hamburger meat in accordance with a method of this invention. The results also show that compounds of Table 2 with structural similarity to those effective according to this invention but differing in the assignments of X and/or n in the formula were ineffective.

I claim:

1. The method of determining the effectiveness of an agent for the relief of elevated blood pressure in a person comprising the steps of
   a) administering to a susceptible person a quantity of a trigger substance, which is a meat product or a product increasing body cholesterol levels, reproducibly effective in producing within a period of six hours a perceptible increase in blood pressure lasting for at least twenty-four hours in the absence of treatment,
   b) administering to said person receiving said quantity of trigger substance a predetermined quantity of the agent whose effectiveness is to be determined,
   c) measuring the duration of said elevation of blood pressure upon administering said agent, and
   d) comparing the duration of said elevation with and without the administration of said agent, an effective agent being one that reduces to three hours maximum the duration of said elevation of blood pressure before returning to normal level.

2. The method of claim 1 in which said trigger substance and said agent are administered simultaneously.

3. The method of claim 1 in which said agent is administered between one minute and three hours after the administration of said trigger substance.

4. The method of claim 1 in which said agent is administered prior to the administration of said trigger substance.

5. The method of claim 1 in which the quantity of trigger substance is in the range from 50 grams to 500 grams.

6. The method of relieving elevation of the blood pressure in a person in need of such relief, comprising the administration to such person of a quantity of an agent which is at least one nutrient compound having the formula

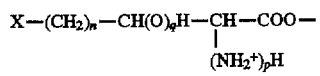

in which X is selected from the group consisting of —CONH$_2$, —NH$_2$, and

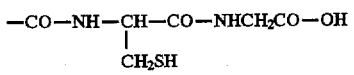

n is zero, one, two, or three, and p being one and q being zero, and —N(CH$_3$)$_{3+}$, p being zero and q being one.

7. The method of claim 6 in which X is —CONH$_2$ and n is one.

8. The method of claim 6 in which X is —NH$_2$ and n is two.

9. The method of claim 6 in which X is —NH$_2$ and n is three.

10. The method of claim 6 in which X is —N(CH$_3$)$_{3+}$, n is zero, p is zero, and q is one.

11. The method of claim 6 in which X is

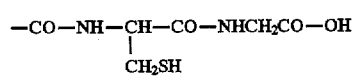

and n is one.

12. A palatable oral dosage form for relieving elevation of the blood pressure in a person in need of such relief comprising a carrier and a quantity of an agent which is at least one nutrient compound having the formula

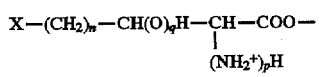

in which X is selected from the group consisting of —CONH$_2$,

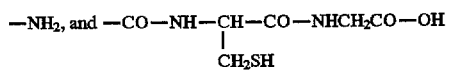

n is zero, one, two, or three, and p being one and q being zero, and —N(CH$_3$)$_{3+}$, p being zero and q being one.

13. A palatable oral dosage form according to claim 12 in which the agent comprises a compound in which X is —N(CH$_3$)$_{3+}$, n is zero, p is zero, and q is one.

14. A palatable oral dosage form according to claim 12 in which the agent comprises a compound in which X is —CONH$_2$ and n is one.

15. A palatable oral dosage form according to claim 12 in which the agent comprises a compound in which X is —NH$_2$ and n is two or three.

16. A palatable oral dosage form according to claim 12 in which the agent comprises a compound in which X is $$-CO-NH-\underset{\underset{CH_2SH}{|}}{CH}-CO-NHCH_2CO-OH$$

and n is one.

17. A palatable oral dosage form according to claim 12 selected from the group consisting of a tablet, a gelatin capsule, a soup, and a fruit flavored drink.

18. A palatable oral dosage form according to claim 12 in which the proportions of carrier to agent are in the range of 4:1 to 1:4.

19. A palatable oral dosage form according to claim 12, in which the carrier is at least one naturally occurring carbohydrate.

20. A palatable oral dosage form according to claim 19, in which the carrier comprises lactose, sucrose, fructose, starch, or cellulose.

21. A palatable oral dosage form according to claim 12, in which the carrier comprises at least one ingestible mineral substance.

22. A palatable oral dosage form according to claim 21, in which the carrier comprises an alkaline earth metal carbonate or alkaline earth metal silicate.

23. A palatable oral dosage form according to claim 12, in which the carrier comprises at least one lipid.

24. A palatable oral dosage form according to claim 23, in which the carrier comprises lecithin or a fatty oil.

25. A palatable oral dosage form according to claim 12 in which the quantity of agent is in the range of 200 to 20000 milligrams.

26. A pleasant tasting oral dosage form according to claim 12, comprising an added flavorant.

27. A pleasant tasting oral dosage form according to claim 26, in which the flavorant is selected from the group consisting of herbs, spices, and essential oils.

28. A pleasant tasting oral dosage form for relieving elevation of the blood pressure in a person in need of such relief comprising a carrier, at least one first nutrient compound having the formula $$X-(CH_2)_n-CH(O)_qH-\underset{\underset{(NH_2^+)_pH}{|}}{CH}-COO-$$

in which X is $-NH_2$, n is two or three, p is one and q is zero, and at least one second nutrient compound having the formula $$X-(CH_2)_n-CH(O)_qH-\underset{\underset{(NH_2^+)_pH}{|}}{CH}-COO-$$

in which X is selected from the group consisting of $-CONH_2$, and $$-CO-NH-\underset{\underset{CH_2SH}{|}}{CH}-CO-NHCH_2CO-OH,$$

n is zero or one, and p being one and q being zero and $-N(CH_3)_{3+}$, p being zero and q being one.

29. The composition of claim 28 in which the proportions of first nutrient compound and second nutrient compound are in the range from 4:1 to 1:4.

* * * * *